(12) United States Patent
Bradley et al.

(10) Patent No.: US 9,546,984 B2
(45) Date of Patent: Jan. 17, 2017

(54) SYSTEM AND METHOD FOR CLEANING A COUPLANT DURING ULTRASONIC TESTING

(71) Applicant: The United States of America as represented by the Secretary of the Navy, Washington, DC (US)

(72) Inventors: Robert E. Bradley, Odon, IN (US); James Rumple, Jasonville, IN (US); John Whitner, Bedford, IN (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 361 days.

(21) Appl. No.: 14/189,338

(22) Filed: Feb. 25, 2014

(65) Prior Publication Data

US 2015/0241396 A1    Aug. 27, 2015

(51) Int. Cl.
*G01N 29/28* (2006.01)

(52) U.S. Cl.
CPC .............. *G01N 29/28* (2013.01); *Y10T 29/494* (2015.01)

(58) Field of Classification Search
CPC ...................................................... G01N 29/28
See application file for complete search history.

(56) References Cited

U.S. PATENT DOCUMENTS

| | | | | |
|---|---|---|---|---|
| 3,939,101 | A | * | 2/1976 | Molina ................. G01N 29/28 252/301.19 |
| 6,220,099 | B1 | * | 4/2001 | Marti ................... G01N 29/226 73/633 |
| 6,725,721 | B2 | * | 4/2004 | Venczel ................. G01N 29/27 73/622 |
| 9,217,729 | B2 | * | 12/2015 | Gruca ................... G01N 29/225 |
| 2009/0249879 | A1 | * | 10/2009 | Jeyaraman ......... G01N 29/0645 73/644 |

* cited by examiner

*Primary Examiner* — Paul West
*Assistant Examiner* — Xin Zhong
(74) *Attorney, Agent, or Firm* — Christopher A. Monsey

(57) ABSTRACT

Methods and systems for cleaning an acoustical couplant and test article before and during ultrasonic testing using components which are used for precleaning the test article as well as cleaning the acoustical couplant during the ultrasonic testing is provided. The invention also provides additional functionality such as preserving the acoustical couplant before, during, and after the ultrasonic testing from loss such as, e.g., evaporation.

20 Claims, 3 Drawing Sheets

SYSTEM AND METHOD FOR CLEANING A COUPLANT DURING ULTRASONIC TESTING

STATEMENT REGARDING FEDERALLY SPONSORED RESEARCH OR DEVELOPMENT

The invention described herein was made in the performance of official duties by employees of the Department of the Navy and may be manufactured, used and licensed by or for the United States Government for any governmental purpose without payment of any royalties thereon.

BACKGROUND AND SUMMARY OF THE INVENTION

The present invention relates generally to a system for cleaning a fluid, e.g., a couplant during submersion ultrasonic testing. More specifically, the present disclosure relates to a system for improved and more consistent test results during ultrasonic testing by constantly filtering and cleaning a couplant used during testing and thereby reducing interference with sound waves used during ultrasonic testing.

Past methods of testing had error problems related to suspended particles in the water. A couplant had to be disposed of in particular ways due to explosive residue or some other hazardous waste. Experimentation has shown a need to avoid making changes to testing processes so testing data always correlates due to consistent test methodology. An effort and cost of disposal of a couplant and solid contaminates is also a significant problem of ultrasonic testing. The need to reduce waste output further motivated a change and improvement in existing processes.

Generally, embodiments of the invention include methods and systems for cleaning an acoustical couplant and test article before and during ultrasonic testing using components which are used for pre-cleaning the test article as well as cleaning the acoustical couplant during the ultrasonic testing is provided. The invention also provides additional functionality such as preserving the acoustical couplant before, during, and after the ultrasonic testing from loss such as, e.g., evaporation.

According to an illustrative embodiment of the present disclosure, a pump is connected via plumbing to a strainer and a filter, through which a couplant from a holding tank passes before flowing through a test tank, where the ultrasonic testing is performed, and a plate cleaning tank, which allows the parts which are to be tested to be cleaned prior to beginning the test, further reducing the amount of residue present in the couplant during testing. Said filter captures contaminants from the cleaning and test operations and said pump moves a couplant through cleaning brushes and said ultrasonic test tank. This filtration system cleans a couplant during testing to eliminate contamination and improves both the quality and consistency of repeated tests. It has the further benefit of extending the useful life of a couplant used during testing thus reducing hazardous waste and reducing time required to remove and dispose of a dirty couplant. A method of manufacturing and method of use is also provided.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

Ultrasonic testing can be used as a method of flaw detection or measurement of material thickness by the use of sound waves. Sound waves are generated by a transducer and are aimed at the target area on a test article. Sound waves are reflected and return to the transducer. A measurement device takes the reflected sound waves and calculates a distance to a flaw or to a thickness of a test article's material at a specific point. By taking measurements at various points a reference can be created to the test article's material thickness and a measurement of any change to the thickness caused by machining or other external forces.

Ultrasonic testing requires a couplant material such as, for example, water. The sound waves travel through the couplant water at a specific velocity. When the sound wave encounters a water-to-test-article-interface, a pulse is reflected to the transducer. This reflection can be measured to indicate a closest surface. The sound waves continue through the test article until it encounters another interface change. This interface change can be a test-article-to-water-interface on an opposite side of the test article than the first interface change. Another pulse is then reflected to the transducer. These two pulses are used to calculate a test article thickness at this point. The test article material's type, composition, shape, and the condition of the couplant and transducer's tip affect quality of measurement.

Figure 1:
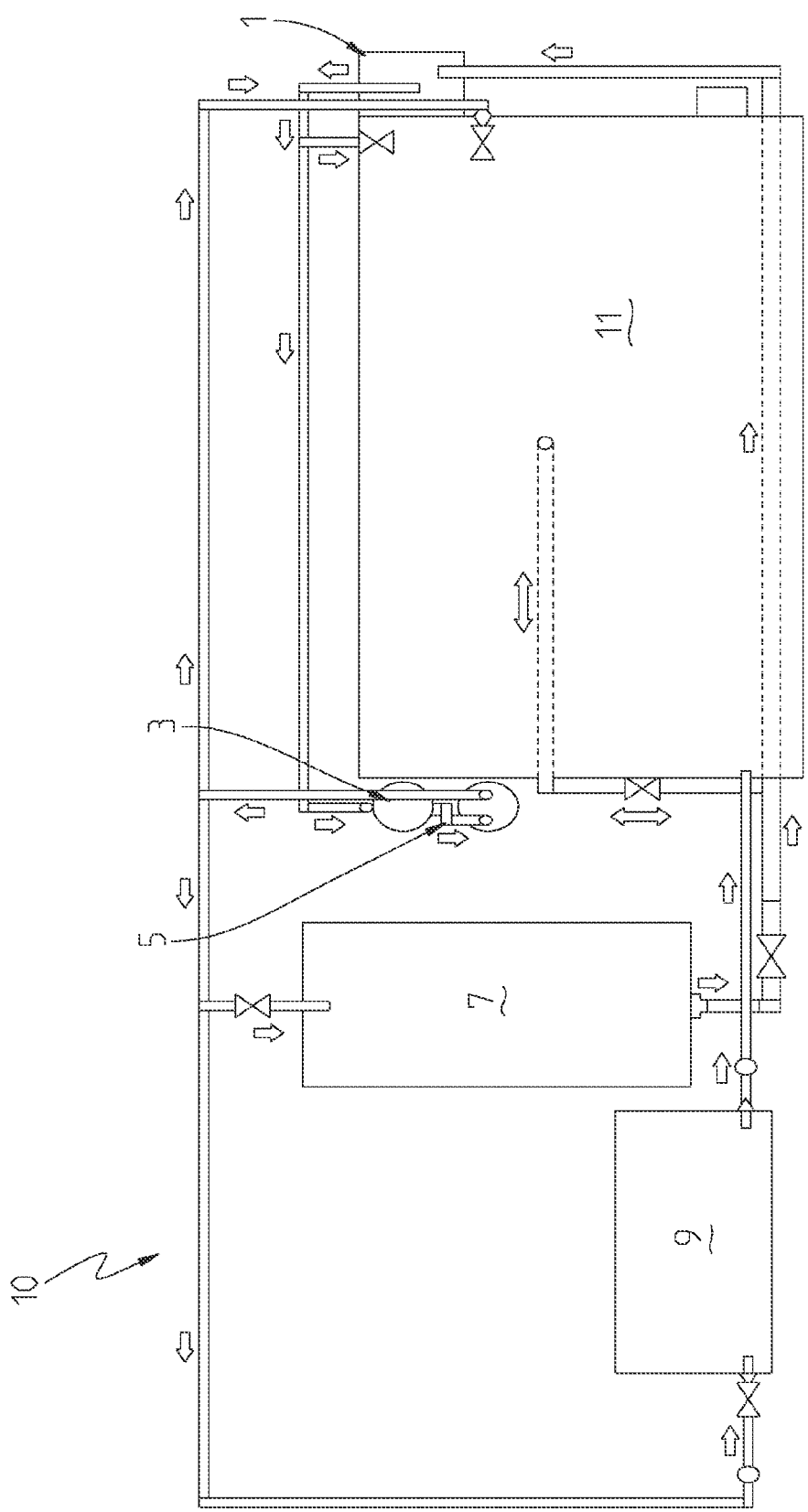
FIG. 1 shows an exemplary top view functional diagram of an exemplary couplant and test article cleaning and testing system.

Referring to FIG. 1, an ultrasonic testing system is provided 10, including cleaning system, that includes a pump 1 which cycles an acoustical couplant/cleaner, e.g., water, through a strainer 3 and a filter 5 which are capable of filtering particles down to e.g., 0.1-10 microns. The couplant/cleaner is then pumped through a holding tank 7, a test tank 9, and test article pre-cleaning tank 11. The test article pre-cleaning tank 11 is used prior to placing the test article in the test tank 9, which includes an ultrasonic testing unit, in order to further reduce the potential for contaminants prior to and during testing. Once the test article has been satisfactorily pre-cleaned, it is placed in the test tank 9 which includes the ultrasonic probe (not shown) which is positioned into the test tank 9 with respect to the test article (not shown) where submersion ultrasonic testing is performed, while the filtered acoustical couplant/cleaner, e.g., water, is pumped constantly through the test tank 9 and the test article pre-cleaning tank 11. The test tank 9 also includes a couplant/cleaner level control mechanism for maintaining a constant level of couplant/cleaner in the test tank 9. In one embodiment, the constant level is maintained by the level control mechanism that can include a stand pipe which permits couplant/cleaner to flow up to the top of the pipe's opening then couplant/cleaner pours into the pipe opening and permits excess couplant/cleaner to flow into the test article pre-cleaning tank 11 where it then is circulated through the strainer 3 and filter 5 for reuse and flow back to the test tank 9 to facilitate ultrasonic testing. The level control mechanism for maintaining a constant level of couplant/cleaner (not shown) can be adjustable to permit different levels of couplant/cleaner within the test tank 9. For example, one embodiment can include multiple removable or adjustable stand pipes which raise or lower the couplant/cleaner level.

The clean couplant/cleaner ensures more accurate and more consistent test results and increases the effective life of said couplant which permits dual use of the couplant for both cleaning and as suitable acoustical medium for the ultrasonic testing while also providing a contaminant removal system that is used by both the pre-cleaning system as well as the ultrasonic testing system. The invention also provides a feature of reducing loss of the couplant/cleaner medium by use, in part, of the holding tank 7 which prevents evaporation while the system 10 is not in used.

The invention also permits use of adjustable position ultrasonic probes (not shown) which can be positioned at various heights and orientations with respect to a test article within the test tank 9. Different sizes, shapes, or thicknesses of a test article can require a reconfiguration of the test tank 9 and the ultrasonic probe as a distance off a surface of the test article must be a specific distances with respect to the ultrasonic probe (not shown).

Figure 2:
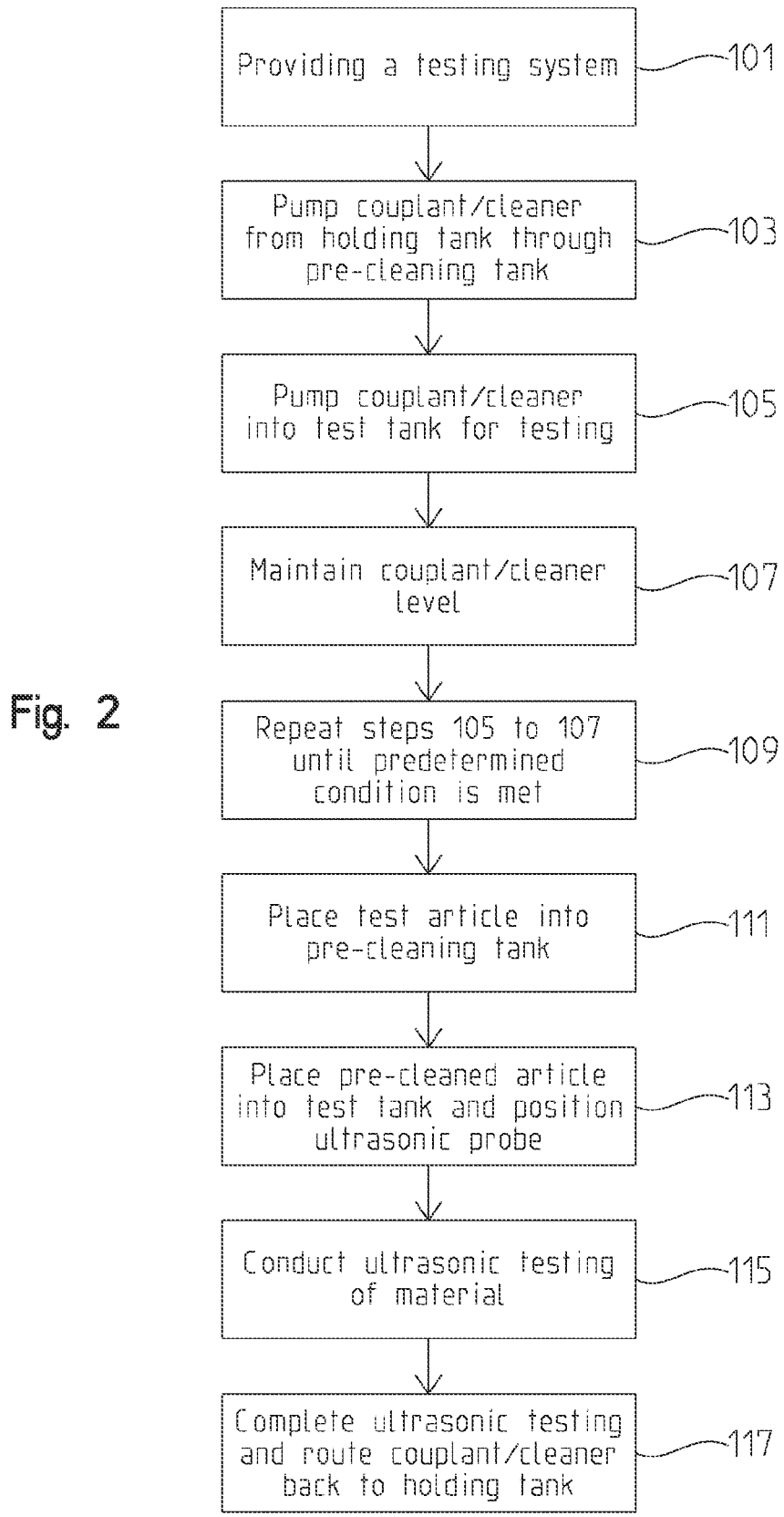
FIG. 2 shows a method of use of an exemplary embodiment of the invention.

FIG. 2 shows an exemplary embodiment of a method in accordance with one embodiment of the invention. For example, a method for conducting ultrasonic testing includes step 101: providing a testing system such as described above. Step 103 is pumping the couplant/cleaner, e.g. water, from the holding tank 7 into the test article pre-cleaning tank 11. Step 105: Pumping the couplant/cleaner through the strainer and filter from the pre-cleaning tank 11 into the test tank 9 for use in ultrasonic testing; Step 107: maintaining a predetermined couplant/cleaner level within the test tank 9 by the couplant/cleaner level control mechanism whereby the couplant/cleaner level control mechanism routes excess couplant/cleaner from the test tank 9 back to the pre-cleaning tank 11 and so maintain the predetermined couplant/cleaner level. Step 109: Repeating steps 105 to 107 until a predetermined condition is met such as Step 117 completion of ultrasonic testing and return of couplant/cleaner to the holding tank 7. Step 111: placing a test article into the pre-cleaning tank 11 to pre-clean the test article, remove contaminants from the test article by use of the couplant/cleaner then removing the contaminants at repeated step 105. Step 113: Placing the pre-cleaned test article into the test tank 9, positioning the ultrasonic probe with respect to the test article to maintain a predetermined distance and orientation to the test article, removing any additional contaminants dislodged by ultrasonic testing by continuously flowing couplant/cleaner as in step 109. Step 115: Conducting ultrasonic testing of the test article using the ultrasonic probe and the couplant/cleaner. Step 117: Completing ultrasonic testing of the test article and routing the couplant/cleaner back to the holding tank 7 from the pre-cleaning tank 11.

Figure 3:
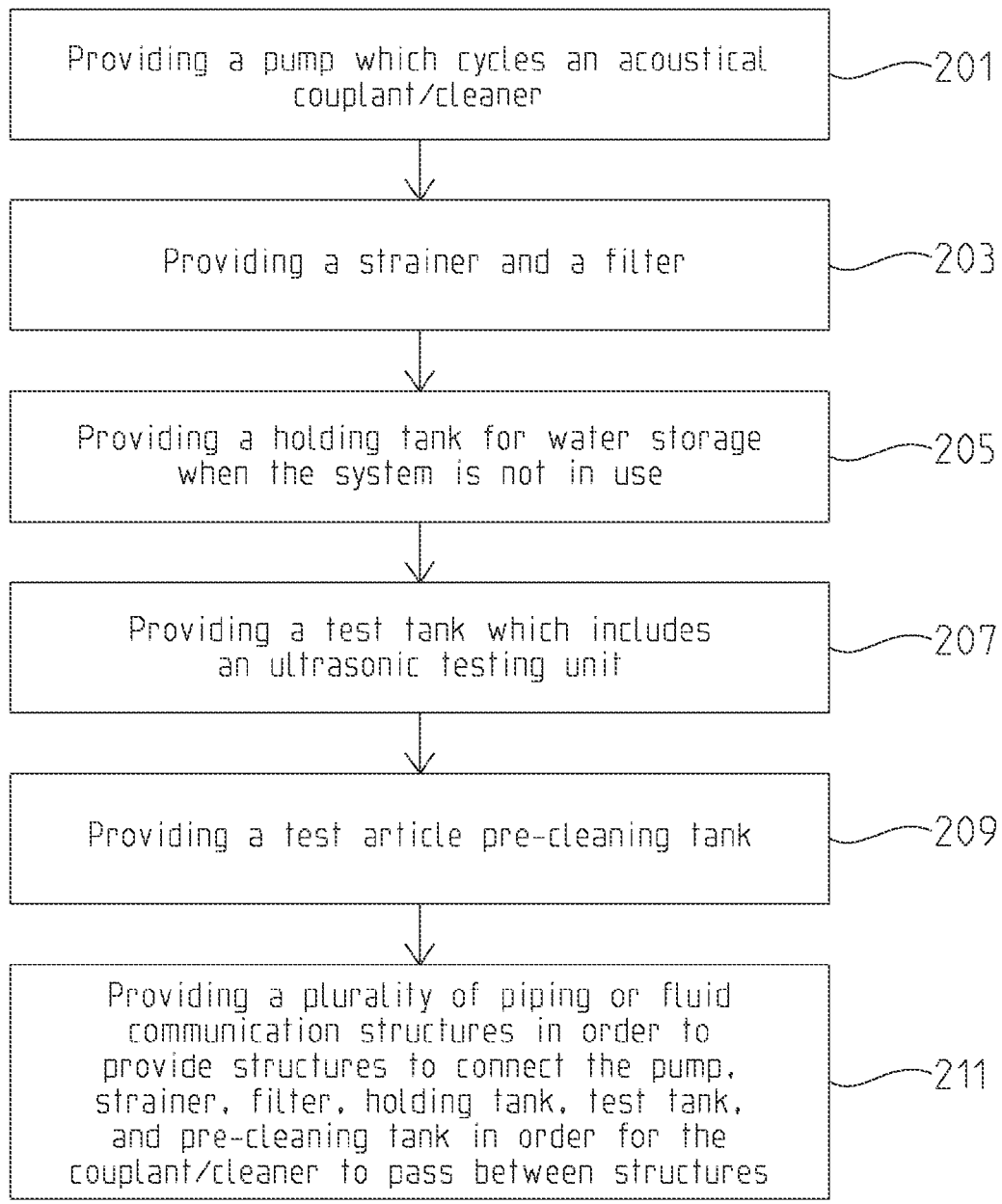
FIG. 3 shows a method of manufacture of an embodiment of the invention such as shown in FIG. 1.

FIG. 3 shows an exemplary method of manufacturing an embodiment of the invention. At Step 201, providing a pump 1 which cycles an acoustical couplant/cleaner, e.g., water. At Step 203, providing a strainer 3 and a filter 5 which are capable of filtering particles down to e.g., 0.1 micron. At Step 205, providing a holding tank 7, for water storage when the system 10 is not in use. At Step 207, providing a test tank 9, including an ultrasonic testing unit (not shown). At Step 209, providing a test article pre-cleaning tank 11 used prior to placing the test article in the test tank 9, in order to further reduce the potential for contaminants prior to and during testing. At Step 211, providing a plurality of piping or fluid communication structures and disposing and coupling one of said plurality of piping or fluid communications structures so as to provide structures to connect said pump 1, strainer 3, filter 5, holding tank 7, test tank 9, and pre-cleaning tank 11 so as to enable said couplant/cleaner to pass between structures in system 10.

Although the invention has been described in detail with reference to certain preferred embodiments, variations and modifications exist within the spirit and scope of the invention as described and defined in the following claims.

The invention claimed is:

1. A system for using, cleaning, and storing a fluid used during ultrasonic testing, comprising:
    a pump;
    a strainer connected to said pump;
    a filter connected to said strainer, wherein said strainer and said filter are configured to remove contaminants from said fluid;
    a holding tank selectively connected to an output of said filter adapted to receive said fluid;
    a test article pre-cleaning tank selectively connected to an input of said pump and a selective input of said holding tank, said test-article pre-cleaning tank is operable to receive and hold said fluid from said holding tank, said pre-cleaning tank is further adapted to receive a test article for immersive cleaning of said contaminants from said test article;
    a test tank selectively connected to said filter, said test tank further comprises an ultrasonic testing structure adapted to perform said ultrasonic testing that is adapted to be repositionable in different locations and orientations relative to a test article disposed within said test tank, said test tank further comprising a test article holding appliance adapted to hold said test article during said ultrasonic testing in a predetermined orientation and distance under said fluid's surface based on a predetermined ultrasonic test parameter, said test tank further comprising a fluid level adjustment structure adapted to permit alteration of a volume of said fluid within said test tank, said level adjustment structure is further adapted to control outflow of said fluid from said test tank into said test article pre-cleaning tank;
    a plurality of valves and a plurality of fluid communication structures or coupling sections, wherein one of said plurality of fluid communication structures are disposed and coupled between each of said pump, strainer, filter, holding tank, test tank and test article pre-cleaning tank, wherein one of said plurality of valves are disposed between an output of said filter and inputs of said test article pre-cleaning tank, said test tank, and said holding tank, wherein another one of said plurality of valves are disposed between an input to said pump and outputs from said test article pre-cleaning tank and said holding tank, wherein said plurality of valves and pump are configured to cooperatively evacuate and isolate said fluid from said test tank and said test article pre-cleaning tank into said holding tank;

wherein said strainer and filter are further adapted to remove said contaminants from said fluid as said fluid is selectively circulated through at least some elements of said system for using, cleaning, and storing a fluid used during ultrasonic testing.

2. The system of claim 1, wherein said filter removes said contaminants comprising particles from 0.1 to 10 microns.

3. The system of claim 1, wherein said fluid comprises water.

4. The system of claim 1, wherein said level adjustment structure comprises an adjustable standpipe disposed within said test tank and coupled to an outflow section from said test tank that is itself coupled to said pre-cleaning tank to receive outflow of said fluid.

5. A system as in claim 1, wherein said predetermined ultrasonic test parameter comprises a size, shape, or thicknesses of said test article.

6. A method of using, cleaning, and storing a fluid used during ultrasonic testing, comprising:
   providing a system for using, cleaning, and storing a fluid used during ultrasonic testing, comprising
      a pump;
      a strainer connected to said pump;
      a filter connected to said strainer;
      a holding tank connected to said filter adapted to receive a fluid;
      a test article pre-cleaning tank connected to said pump and said holding tank, said test-article pre-cleaning tank is operable to receive and hold said fluid from said holding tank, said pre-cleaning tank is further adapted to receive a test article for immersive cleaning of contaminants comprising particles from said test article;
      a test tank connected to said filter, said test tank further comprises an ultrasonic testing structure adapted to perform said ultrasonic testing of said test article that is adapted to be repositionable in different locations and orientations relative to said test article disposed within said test tank, said test tank further comprising a test article holding appliance adapted to hold said test article during said ultrasonic testing in a predetermined orientation and distance under said fluid's surface based on a predetermined ultrasonic test parameter, said test tank further comprising a fluid level adjustment structure adapted to permit alteration of a volume of said fluid within said test tank, said fluid level adjustment structure is further adapted to control outflow of said fluid from said test tank into said test article pre-cleaning tank;
      a plurality of fluid communication structures or coupling sections, wherein one of said plurality of fluid communication structures are disposed and coupled between each of said pump, strainer, filter, holding tank, test tank and test article pre-cleaning tank;
   wherein said strainer and filter are further adapted to remove said contaminants from said fluid as it is circulated through said system;
   pumping said fluid from said holding tank into said test article pre-cleaning tank;
   pumping said fluid through said strainer and said filter from said test article pre-cleaning tank into said test tank for use in ultrasonic testing of said test article;
   maintaining said predetermined level of said fluid within said test tank by said fluid level adjustment structure based on said predetermined ultrasonic test parameter;
   placing said test article into said test article pre-cleaning tank for said contaminant removal;
   removing said test article from said test article pre-cleaning tank and placing said test article into said test tank for said ultrasonic testing;
   conducting said ultrasonic testing of said test article; and
   completing said ultrasonic testing of said test article and routing said fluid back to said holding tank from said pre-cleaning tank and said test tank and thereby removing said fluid from said test tank and said pre-cleaning tank and isolating said fluid in said holding tank to prevent evaporation of said fluid from said holding tank.

7. A method of claim 6, wherein said fluid comprises water.

8. A method of claim 6, wherein said fluid level control mechanism routes excess fluid from said test tank back to said pre-cleaning tank during cleaning or testing operations.

9. A method of manufacture of a system for using, cleaning, and storing a fluid used during ultrasonic testing, comprising:
   providing a strainer and a filter fluidly coupled to an output area or section of said strainer, wherein strainer and filter are adapted to capture contaminants comprising particles from a fluid adapted for cleaning and ultrasonic testing of a test article;
   providing a holding tank for said fluid;
   providing a test tank, wherein said test tank is configured to hold said test article submerged in said fluid, said test tank further includes an ultrasonic testing unit comprising a sound wave generator configured to direct an ultrasonic emission against one or more test interface sections of the test article and determine a plurality of test article characteristics comprising test article thickness in different sections of said test interface sections, said test tank is further configured with a fluid level control system configured to maintain a predetermined level of said fluid in said test tank suitable to ensure said fluid submerges said test article;
   providing a test article pre-cleaning tank comprising a test article cleaning system comprising a structure to receive and apply said fluid against said test article to remove said contaminants introduced into said fluid from said test article, wherein an outflow or output from said fluid level control system in said test tank is fluidly coupled with said pre-cleaning tank to drain said fluid into said pre-cleaning tank;
   providing a first, second, third, and fourth, and fifth valve configured to selectively permit or halt flow of said fluid through said valves;
   providing a pump with a pump input fluidly coupled to an output of said first valve, an input of said first valve is fluidly coupled with an output of said holding tank, said pump further comprises a pump output fluidly coupled to an input of said strainer, wherein an output of said filter is fluidly coupled to said second, third, and fourth valves, wherein said second valve is selectively fluidly coupled to said holding tank, third valve is selectively fluidly coupled to said test tank, and said fourth valve is selectively fluidly coupled to said article pre-cleaning tank, wherein said first, second, third, and fourth valves are configured to selectively convey or block conveyance of said fluid to said holding tank, said pre-cleaning tank, or said test tank, wherein said first, second, third, fourth and fifth valves are further configured to cooperate with said pump to selectively convey and isolate said fluid from said test tank and said article pre-cleaning tank to said holding tank to prevent evaporation of holding tank contents comprising said fluid within the holding tank, wherein said fifth valve is further bi-directionally, selectively, and fluidly coupled with said test article pre-cleaning tank, wherein an output from said fifth valve is further selectively fluidly coupled with said input into said pump.

10. A method of claim 9, wherein said filter removes said particles from 0.1 to 10 microns.

11. A method of claim 9, wherein said fluid comprises water.

12. A method of claim 9, wherein said ultrasonic testing structure is adapted to perform said ultrasonic testing, said ultrasonic testing structure is adapted to be repositionable in different locations and orientations relative to said test article disposed within said test tank, said test tank further comprising a test article holding appliance adapted to hold said test article during said ultrasonic testing in a predetermined orientation and distance under said fluid's surface based on a predetermined ultrasonic test parameter, said fluid level control system in said test tank is further adapted to selectively enable alteration of a volume of said fluid within said test tank, said fluid level control system further includes a level adjustment structure that to controls outflow of said fluid from said test tank into said test article pre-cleaning tank.

13. A method as in claim 9, wherein said test-article pre-cleaning tank is operable to receive and hold said fluid from said holding tank, said pre-cleaning tank is further adapted to receive a test article for immersive cleaning of said contaminants from said test article.

14. A method as in claim 9, wherein said strainer and filter are further adapted to remove said contaminants from said fluid as it is circulated through at least one section of said system.

15. A system usable for using, cleaning and storing fluid used in ultrasonic testing, comprising:
providing a strainer and a filter fluidly coupled to an output area or section of said strainer, wherein strainer and filter are adapted to capture contaminants comprising particles from a fluid adapted for cleaning and ultrasonic testing of a test article;
providing a holding tank for said fluid;
providing a test tank, wherein said test tank is configured to hold said test article submerged in said fluid, said test tank further includes an ultrasonic testing unit comprising a sound wave generator configured to direct an ultrasonic emission against one or more test interface sections of the test article and determine a plurality of test article characteristics comprising test article thickness in different sections of said test interface sections, said test tank is further configured with a fluid level control system configured to maintain a predetermined level of said fluid in said test tank suitable to ensure said fluid submerges said test article;
providing a test article pre-cleaning tank comprising a test article cleaning system comprising a structure to receive and apply said fluid against said test article to remove said contaminants from said test article, wherein an outflow or output from said fluid level control system in said test tank is fluidly coupled with said pre-cleaning tank;
providing a first, second, third, and fourth, and fifth valve configured to selectively permit or halt flow of said fluid through said valves;
providing a pump with a pump input fluidly coupled to an output of said first valve, an input of said first valve is fluidly coupled with an output of said holding tank, said pump further comprises a pump output fluidly coupled to an input of said strainer, wherein an output of said filter is fluidly coupled to said second, third, and fourth valves, wherein said second valve is selectively fluidly coupled to said holding tank, third valve is selectively fluidly coupled to said test tank, and said fourth valve is selectively fluidly coupled to said article pre-cleaning tank, wherein said first, second, third, and fourth valves are configured to selectively convey or block conveyance of said fluid to said holding tank, said pre-cleaning tank, or said test tank, wherein said first, second, third, fourth and fifth valves are further configured to cooperate with said pump to selectively convey and isolate said fluid from said test tank and said article pre-cleaning tank to said holding tank to prevent evaporation of holding tank contents comprising said fluid within the holding tank, wherein said fifth valve is further bi-directionally, selectively, and fluidly coupled with said test article pre-cleaning tank, wherein an output from said fifth valve is further selectively fluidly coupled with said input into said pump.

16. A system as in claim 15, wherein said filter removes said contaminants comprising said particles from 0.1 to 10 microns.

17. A system as in claim 16, wherein said fluid comprises water.

18. A system as in claim 16, wherein said ultrasonic testing structure is adapted to perform said ultrasonic testing of said test article, said ultrasonic testing structure is adapted to be repositionable in different locations and orientations relative to said test article disposed within said test tank, said test tank further comprising a test article holding appliance adapted to hold said test article during said ultrasonic testing in a predetermined orientation and distance under said fluid's surface based on a predetermined ultrasonic test parameter, said fluid level control system in said test tank further adapted to permit alteration of a volume of said fluid within said test tank, said level adjustment structure is further adapted to control outflow of said fluid from said test tank into said test article pre-cleaning tank.

19. A method as in claim 16, wherein said test-article pre-cleaning tank is operable to receive and hold said fluid from said holding tank, said pre-cleaning tank is further adapted to receive a test article for immersive cleaning of said contaminants from said test article.

20. A method as in claim 16, wherein said strainer and filter are further adapted to remove said contaminants from said fluid as it is circulated through at least some elements of said system for using, cleaning, and storing a fluid used during ultrasonic testing.

* * * * *